United States Patent [19]
Bowlin

[11] Patent Number: 6,010,573
[45] Date of Patent: Jan. 4, 2000

[54] APPARATUS AND METHOD FOR ENDOTHELIAL CELL SEEDING/ TRANSFECTION OF INTRAVASCULAR STENTS

[75] Inventor: Gary L. Bowlin, Mechanicsville, Va.

[73] Assignee: Virginia Commonwealth University, Richmond, Va.

[21] Appl. No.: 09/108,984

[22] Filed: Jul. 1, 1998

[51] Int. Cl.[7] .............................. B05C 3/02; B05D 3/14; C12N 13/00; C12N 15/00
[52] U.S. Cl. ................... 118/620; 118/621; 118/622; 118/638; 118/408; 118/409; 118/416; 427/2.11; 427/2.12; 427/2.28; 427/178; 427/346; 427/435; 427/457; 427/481; 435/173.1; 435/173.2; 435/173.4; 435/173.5; 435/173.6; 435/174; 435/176; 435/283.1; 435/285.2
[58] Field of Search ................... 118/621, 622, 118/638, 52, 55, 408, 409, 416, 620; 435/173.1, 173.2, 173.4, 173.5, 173.6, 174, 177, 180, 283.1, 285.2, 176; 427/481, 2.1, 2.11, 2.28, 2.24, 177, 178, 289, 346, 457, 435

[56] References Cited

U.S. PATENT DOCUMENTS

| | | | |
|---|---|---|---|
| 4,499,118 | 2/1985 | Dietz et al. | 427/481 |
| 4,512,896 | 4/1985 | Gershoni | 210/635 |
| 4,688,239 | 8/1987 | Schaffner et al. | 378/141 |
| 4,939,151 | 7/1990 | Bacehowski et al. | 435/284 |
| 4,972,569 | 11/1990 | Aoki et al. | 427/481 |
| 5,037,378 | 8/1991 | Muller et al. | 600/36 |
| 5,037,676 | 8/1991 | Petropoulos et al. | 427/481 |
| 5,078,736 | 1/1992 | Behl | 623/1 |

(List continued on next page.)

OTHER PUBLICATIONS

Dotter et al., Transluminal Treatment of Arteriosclerotic Obstruction, Circulation, Vol. XXX (Nov. 1964), pp. 654–670.

Graham et al., Expanded Polytetrafluoroethylene Vascular Prostheses Seeded with Enzymatically Derived and Cultured Canine Endothelial Cells, Surgery, vol. 91, No. 5 (May, 1982), pp. 550–559.

Stanley et al., Enhanced Patency of Small–Diameter, Externally Supported Dacron Iliofemoral Grafts Seeded with Endothelial Cells, Surgery, vol. 92, No. 6 (Dec. 1982), pp. 994–1005.

Popov et al, Mechanism of Cell Protrusion Formation in Electrical Field: the role of actin, Biochimica et Bioplysica Acta 1066 (1991), pp. 151–158.

Tian Y. Tsong, Electroporation of Cell Membranes, Biophys. J. Biophysical Society, Vol. 60 (Aug. 1991), pp. 297–306.

Douville et al., Impact of Endothelial Cell Seeding on Long–Term Patency and Subendothelial Proliferation in a Small–Caliber Highly Porous Polytetrafluoroethylene Graft, Journal of Vascular Surgery, vol. 5, No. 4 (Apr. 1978), pp. 544–550.

(List continued on next page.)

*Primary Examiner*—Diana Dudash
*Attorney, Agent, or Firm*—Renner, Kenner, Greive, Bobak, Taylor & Weber

[57] ABSTRACT

An apparatus for modifying an intravascular stent with endothelial cells and/or engineered endothelial cells which may have genetically altered DNA to minimize failure rates includes an external conductor sleeve, an insulating tube held therein, and a pair of insulated end caps, each detachably securable over each end of said insulating tube. Each insulated cap has a substantially centered aperture therethrough and a stent holder extending transversely therefrom to hold opposite ends of the stent therebetween. The insulated end caps and the insulating tube hold a solution containing the endothelial cells inside the insulating tube to surround exposed surfaces of the stent. An insulated internal conductor is received through the apertures. A power source for generating an electrical field between the stent and the external conductor and between the stent and the internal conductor is employed to temporarily alter the electrical charge of the stent to attract and adhere the desired endothelial cells and genetically altered DNA thereto.

22 Claims, 2 Drawing Sheets

U.S. PATENT DOCUMENTS

| | | | |
|---|---|---|---|
| 5,256,141 | 10/1993 | Gencheff et al. | 604/53 |
| 5,304,120 | 4/1994 | Crandell et al. | 604/52 |
| 5,534,387 | 7/1996 | Lukic | 427/2.25 |
| 5,714,359 | 2/1998 | Bowlin et al. | 435/174 |
| 5,723,324 | 3/1998 | Bowlin et al. | 435/173.6 |
| 5,820,917 | 10/1998 | Tuch | 427/2.1 |
| 5,843,741 | 12/1998 | Wong et al. | 435/173.8 |
| 5,939,145 | 8/1999 | Oram | 427/407.1 |

OTHER PUBLICATIONS

Dichek et al., Seeding of Intravascular Stents with Genetically Engineered Endothelial Cells, Circulation, vol. 80, No. 5 (Nov. 1987), pp. 1347–1353.

Flugelman et al., Genetically Engineered Endothelial Cells Remain Adherent and Viable After Stent Deployment and Exposure to Flow in Vitro, Circulation Research, vol. 70, No. 2 (Feb. 1992), pp. 348–354.

APPARATUS AND METHOD FOR ENDOTHELIAL CELL SEEDING/ TRANSFECTION OF INTRAVASCULAR STENTS

TECHNICAL FIELD

This invention relates to adhering material to a surface of an in vitro device. In particular, the present invention relates to seeding endothelial cells and transfecting deoxyribonucleic acid (DNA) to the endothelial cells. Specifically, the present invention relates to an apparatus and its method for use for enhancing adhesion of endothelial cells with or without inserted DNA material to inner and outer surfaces of a stent to be inserted into an artery or vein.

BACKGROUND ART

The use of percutaneous transluminal angioplasty (PTA) has become a widely accepted treatment for atherosclerosis which is accumulation of lipids (cholesterol) within the artery wall that blocks the flow of blood through the artery. PTA employs the use of a balloon catheter that is inserted into the femoral artery and guided with a wire into the coronary arteries through the aorta. The balloon portion is placed within a blocked artery and inflated. The balloon is then removed and blood flow through the artery is hopefully improved.

The use of stents in conjunction with PTA has proved beneficial in treating atherosclerosis. The first situation indicative for stent use is that in many cases the PTA procedure, by itself, is unsuccessful in producing an open lumen. Stents are also used where there is the possibility of abrupt vessel closure following the PTA. This abrupt closure is due to the artery wall expanding with the inflation of the balloon, but quickly recoiling after the removal of the intraluminal balloon pressure. The third situation is when chronic restenosis of the treated area occurs within six months to a year after the procedure. In other words, after a period of time, the cellular components within the artery wall, such as the smooth muscle cells, grow out of control and at the same time, produce components which build up much like an atherosclerotic plaque and lead to blockage of the artery. Generally, this blockage occurs within one to five years.

One of the reasons for failure of such an intravascular device is due to the formation of acute, spontaneous thrombosis, and chronic intimal, hyper-plasia. Thrombosis is initiated by platelets reacting with any non-endothelialized foreign surface to initiate a platelet plug. This plug acts as a template for the blood coagulation proteins. Over time, the platelet plug continues to grow, resulting in occlusion, or failure of the intravascular device.

Under normal circumstances, platelets circulate through the vascular system in a non-adherent state. This non-adherence is accomplished by the endothelial cells lining the vascular system. These endothelial cells have several factors which contribute to their non-thrombogenic properties. These factors include, but are not limited to, negative surface charge, the heparin sulfate in their glycocalyx, the production and release of prostacylin, adenosine diphosphate, endothelium-derived relaxing factor, and thrombomodulin. Adherence of more endothelial cells to the intravascular device leads to enhanced healing times and reduced failure rates of the device.

Problems particularly related to the use of stents during PTA procedures are acute thrombosis and chronic restentosis. Acute thrombosis may happen anywhere from two hours after implantation up to thirty days post-implantation. Clotting mechanisms generated by the human body build-up on the stent material within the blood stream and eventually lead to blockage of flow. This build-up is due primarily to the material characteristics of the stent such as surface charge and surface texture and also to the expansion of the stent. Depending upon the type of material used for the stent, the degree of thombogenicity varies. Additionally, expansion of the stent may cause acute thrombosis because of the circumferential expansion of the arterial wall which exposes the sub-endothelium tissue which is highly thrombogenic. To prevent acute thrombotic occlusion, anticoagulant therapy is required. Other problems, such as chronic restentosis or intimal hyperplasia, are typically due to a more rigid stent material contained in a compliant native artery.

The problems encountered with the use of intravascular stents are similar to those encountered with synthetic vascular grafts as discussed in U.S. Pat. Nos. 5,714,359 and 5,723,324 which are incorporated herein by reference. However, these patents only discuss modifying synthetic graft material. In particular, the systems disclosed therein are specifically for seeding luminal or inner wall surfaces of a synthetic non-conductive material and are totally incapable of providing the necessary cell coverage of an outer surface and in the intristicies between the interleaved wire materials which comprise the stent. Moreover, these patents have no appreciation of the need for carrying cell material to an outer surface of the device to be implanted or that a conductive material can be seeded.

Currently used methods for endothelial cell transplantation of stents requires the use of adhesive proteins to enhance endothelial cell adhesion to the surfaces thereof. As is known, stents are typically coated with some type of adhesive protein to make the material more attractive to endothelial cells. Current endothelial cell transplantation techniques may require up to 3 days to transplant endothelial cells and allow for morphological maturation on the surface of the stent.

Another drawback to current cell transplantation techniques is that they require the use of excessive amounts of anticoagulant, thrombolytic or smooth muscle cell antiproliferative agents which are typically delivered through drug therapy. It is also known that endothelial cells may be genetically engineered with the desired properties. However, known methods for transfection and transplation take place in two time consuming steps, typically several days, to achieve maximum efficiencies. This leads to the increased chance for contamination of the stent due to excessive handling.

Therefore, there is a need in the art to seed all surfaces of an intravascular stent with endothelial cells that may be genetically engineered to facilitate acceptance of the stent when implanted and reduce to the occurrence of chronic restentosis and acute thrombosis.

DISCLOSURE OF INVENTION

It is thus an object of the present invention to provide an apparatus and related method for modifying an intravascular stent with material containing endothelial cells and/or genetically modified endothelial cells.

It is another object of the present invention to provide an apparatus in which a cannister assembly is employed to hold an intravascular stent in a suspended position to allow material contained in a solution to contact substantially all inner and outer surfaces and intristicies of the intravascular stent.

It is a further object of the present invention to provide an apparatus, as above, in which a conductor is proximally associated with the cannister assembly.

It is yet another object of the present invention to provide an apparatus, as above, in which a power source for generating an electrical field between the stent and the conductor is employed to temporarily alter the electrical charge of the stent to attract and adhere the material to the stent.

It is yet another object of the present invention to provide an apparatus, as above, to provide an external conductor sleeve which receives therein an insulating material that surrounds the stent.

It is still another object of the present invention to provide an apparatus, as above, in which a pair of insulated end caps are detachably secured to each end of the external conductor and insulating material to contain the solution and hold the stent in an appropriate position.

It is still a further object of the present invention to provide an apparatus, as above, in which each of the insulated end caps have a substantially centered aperture therethrough and a stent holder extending transversely therefrom to hold opposite ends of the stent between the end caps.

It is an additional object of the present invention to provide an apparatus, as above, in which an internal conductor is received through the apertures of the end caps and internally to the stent, wherein both the internal and external conductors are connected to a negative terminal of the power source and wherein the stent via the stent holder is connected to a positive terminal of the power source.

It is still yet another object of the present invention, as above, to provide a motor for rotating the cannister assembly while the power source temporarily alters the electrical charge of the stent.

The foregoing and other objects of the present invention, which shall become apparent as the detailed description proceeds, are achieved by an apparatus for modifying an intravascular stent with material contained in a solution, comprising an external conductor, an insulator received within the external conductor, means for suspending the stent in a spaced apart position within the insulator, the insulator receiving the solution which freely flows in and around the stent, and a power source for generating an electrical field between the stent and the external conductor so that the electrical charge on the stent is temporarily altered to modify the stent with the material in the solution.

Other aspects of the present invention are attained by an apparatus for modifying an intravascular stent with material to minimize failure rates after implantation, comprising an external conductor sleeve, an insulating tube held within the external conductor sleeve, a pair of insulated end caps, each detachably securable over each end of the insulating tube, each insulated cap having a substantially centered aperture therethrough and a stent holder extending transversely therefrom to hold opposite ends of the stent therebetween, wherein the insulated end caps hold a solution containing the material inside the insulating tube to surround exposed surfaces of the stent, an insulated internal conductor receivable within the stent and through the apertures, and a power source for generating an electrical field between the stent and the external conductor and between the stent and the internal conductor to temporarily alter the electrical charge of the stent to attract and adhere the desired material thereto.

Still another object of the present invention is attained by an apparatus for modifying an intravascular stent with material contained in a solution, comprising a canister assembly for holding the intravascular stent in a suspended position to allow the solution to contact substantially all inner and outer surfaces of the intravascular stent, a conductor proximally associated with the cannister assembly, and a power source for generating an electrical field between the stent and the conductor to temporarily alter the electrical charge of the stent to attract and adhere the desired material thereto.

Yet further aspects of the present invention are attained by a method for incorporating material on the inner and outer surfaces of an intravascular stent, comprising the steps of suspending the intravascular stent in a container, filling the container with a solution containing the material, wherein the solution contacts the inner and outer surfaces of the stent, proximally positioning a conductor adjacent the stent, connecting the stent and the conductor to a power source, and temporarily applying an electrical potential with the power source between the intravascular stent and the conductor to alter the surface charge of the stent thereby attracting and incorporating the material onto the intravascular stent.

These and other objects of the present invention, as well as the advantages thereof over existing prior art forms, which will become apparent from the description to follow, are accomplished by the improvements hereinafter described and claimed.

BRIEF DESCRIPTION OF THE DRAWINGS

For a complete understanding of the objects, techniques and structure of the invention, reference should be made to the following detailed description and accompanying drawings, wherein.

BEST MODE FOR CARRYING OUT THE INVENTION

Figure 1:
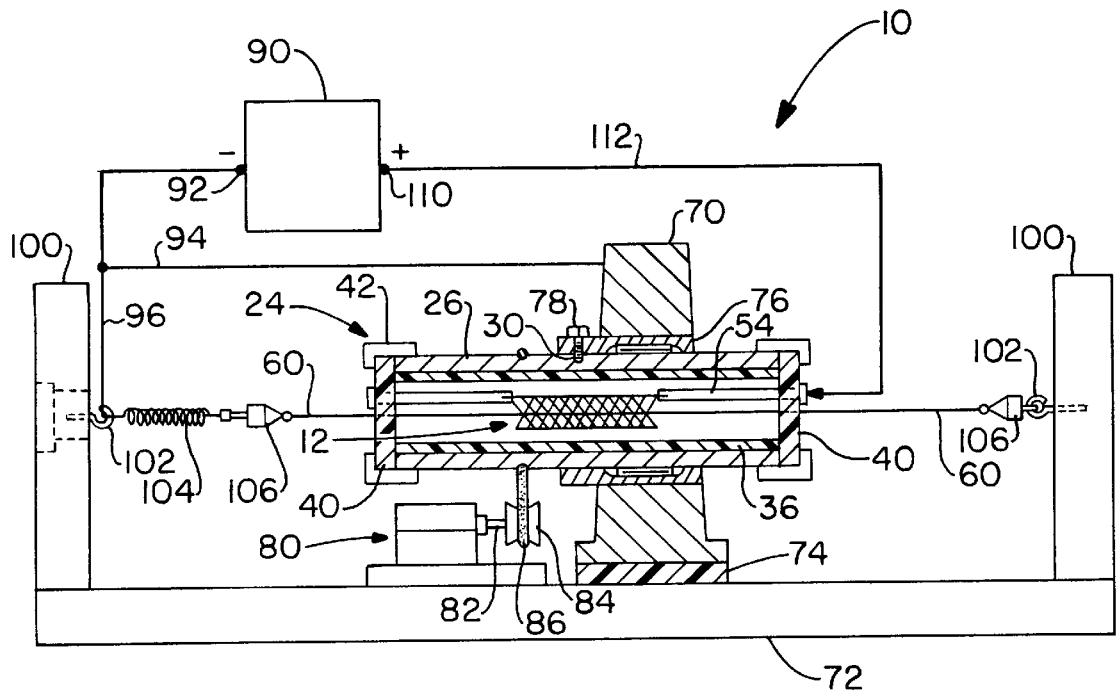
FIG. 1 is a schematic representation of an apparatus according to the present invention.
Figure 2:
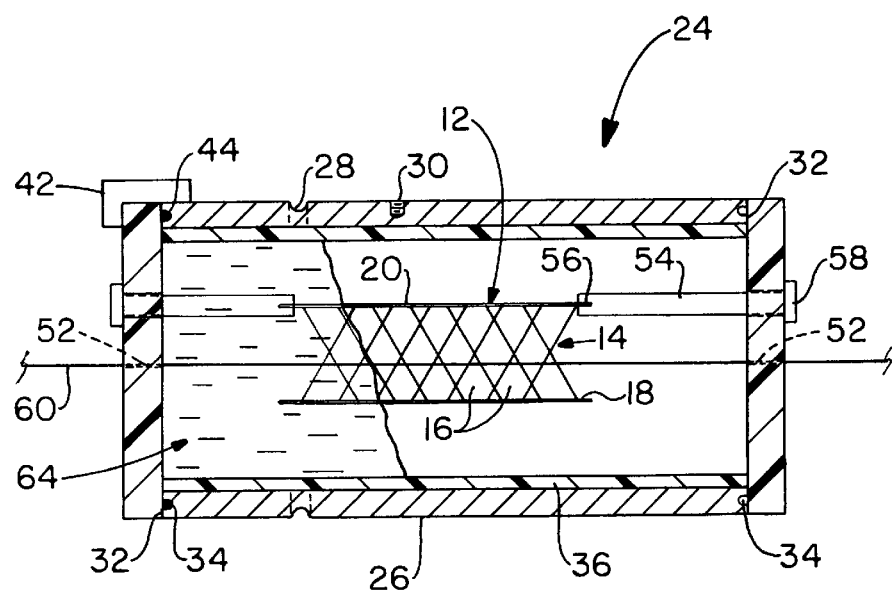
FIG. 2 is an enlarged schematic cross-sectional view of a cannister assembly employed in the present invention.

Referring now to the drawings and in particular to FIGS. 1 and 2, it can be seen that an apparatus for endothelial cell seeding/transfection of intravascular stents is designated generally by the numeral 10. As shown, the apparatus 10 induces a temporary surface charge which facilitates the adhesion of endothelial cells and morphologic maturation on stent surfaces within a clinically acceptable time prior to implantation. The stent 12 is typically of a metallic construction such as 316L stainless steel, tantalum and cobalt-based alloys. All of these materials have very good electrical conduction properties. It will be appreciated that the present invention may be used with stents that are provided with polymer coatings. Stents are usually provided in sizes anywhere from between 2 mm to 15 mm in diameter. Use of the present invention is particularly advantageous with smaller diameter stents because of the need to prevent clot formation which may lead to blood flow blockage.

The stent 12 includes a plurality of interleaved wires 14 made up of the materials specified above. The interleaved wires 14 form openings 16 the size of which depends upon the expansion or contraction of the stent 12. Each stent 12 has an inner surface 18 and an outer surface 20 wherein the outer surface 20 is placed adjacent the blocked area of the artery or vein and then expanded by a catheter balloon (not shown) to allow improved blood flow through the blocked area.

As best seen in FIG. 2, a cannister assembly, designated generally by the numeral 24, is employed to hold and suspend the intravascular stent 12 in at least a somewhat expanded position. The cannister assembly 24 includes an external conductor sleeve 26 which in the preferred embodiment is a stainless steel round. The sleeve 26 is provided with a circumferential groove 28 and a transverse threaded opening 30. The sleeve 26 has a rim 32 at each end which provides an annular end groove 34.

An insulating tube 36, preferably made of Teflon® (Teflon is a registered trademark of E.I. Dupont De Nemours & Co.) is disposed within the sleeve 26. The insulting tube 36 is substantially the same length as the sleeve 26 and is secured in such a manner so that it does not rotate within the sleeve 26. In other words, as the sleeve 26 rotates, the tube 36 rotates. In the preferred embodiment, the thickness of the insulating tube 36 is relatively thin.

A pair of insulated end caps 40 are detachably securable over the respective rims 32 by the use of a clamp 42. Of course, other devices for holding the end caps 40 to the external conductor sleeve 26 and insulating tube 36, such as fasteners, pins, threaded inserts and the like may be employed in place of the clamp 42. An O-ring 44 may be positioned between the end caps 40 and the rims 32 in the annular end grooves 34 to provide a fluid-tight connection between the sleeve 26/tube 36 and the end caps 40.

Each end cap 40 is provided with a central aperture 52 extending therethrough. A stent holder 54, which is preferably made of stainless steel, is secured to each end cap in an off-center position. Although only one stent holder 54 is provided with each end cap 40, it will be appreciated that the holder 54 may be configured with multiple stent holders or any conductive construction which maintains the stent in a substantially concentric position within the insulating tube 36. One end of the stent holder 54 is provided with a slit 56 for receiving a respective end of the stent 12. The stent holder 54 extends through the end cap and is terminated at its opposite end with a conductive pad 58. It will be appreciated that a fluid-tight seal is provided between the stent holder 54 and the end cap 40.

An insulated wire 60, which in the preferred embodiment is a silver-plated copper-coated conductive wire insulated with GORE-TEX® (a registered trademark of W.L. Gore & Associates, Inc.), is positionable through the respective apertures 52. The diameter of the insulated wire is variable depending upon the size of the stent to be seeded and other factors. The apertures 52 are sized to be slightly smaller than the insulated wire 60 to provide a fluid-tight seal therebetween.

In assembling the cannister assembly 24, one insulated end cap 40 is secured to the appropriate end of the insulating tube 36 and external conductor sleeve 26, with one end of the stent 12 positioned in the slit 56. It will be appreciated that the stent 12 is expanded slightly to allow removal of the stent from the catheter. The insulated wire 60 is concentrically positioned through the center of the stent 12 and then threaded through the aperture 52. At this time, a solution 64, which contains the endothelial cells and any additional genetically engineered material, is disposed into the insulated tube 36. The insulated wire 60 is then inserted through the aperture 52 of the opposite end cap 40 while the opposite end of the stent 12 is attached to the slit 56 of the opposite stent holder 54. It will be appreciated that the stent holder 54 may be slidably movable with respect to the end cap 40 to allow proper positioning of the stent 12 within the tube 36. The opposite end cap 40 is then secured to the sleeve 26 and the tube 36 with the clamps 42. It will be appreciated that the cannister assembly 24 could be first assembled and completely secured to properly position the stent 12 therein. The cannister assembly 24 could then be provided with an opening to allow entry of the solution 64 therein to ensure maximum fill of the cannister assembly.

The endothelial cells (EC) used in the solution 64 are resuspended ($5 \times 10^6$ EC/mL) in a Dulbecco's phosphate buffered saline (DPBS) without calcium and magnesium. The transplantation/transfection DPBS contains: antioxidants ($1.3 \times 10^{-3}$M dimethyl sulfoxide, $1 \times 10^{-4}$M sodium ascorbate, and $3.6 \times 10^{-5}$M glutathione) to protect the cellular membranes from free radicals during transplantation; 1% of albumin to increase the DPBS osmotic pressure (~290 mOsm), up to 100 μg/mL DEAE-Dextran to cause the vector (DNA) to stick to the EC membranes; and the foreign DNA to be transfected at the experimentally determined optimum concentration. It will be appreciated that the endothelial cells may also be genetically engineered to produce excessive amounts of anticoagulant, thrombolytic, or a smooth muscle cell antiproliferative agent.

Once the cannister assembly 24 is sealed and the stent 12 is held in a suspended and concentric position therein, the cannister assembly 24 is placed horizontally in a pillow block 70 which allows for rotation of the cannister assembly 24. The pillow block 70 is mounted to abase 72 with an insulator gasket 74 therebetween. The gasket 74 functions to electrically isolate the pillow block from the base 72. A roller bearing 76 is provided within the pillow block 70 to allow rotation of the assembly 24. A set screw 78 is provided to interconnect the bearing 76 to the threaded opening 30 provided in the external sleeve 26. Of course, the cannister assembly 24 could be rotated in a vertical position as long as the stent 12 is fully covered by the solution.

A drive motor 80 is mounted to the base 72 and provides a rotatable shaft 82. A sheave 84 extends from the rotatable shaft 82 to allow for mounting of a drive belt 86 which is received within the annular groove 28.

A power source and controller 90 is electrically connected to the stent 12; the insulated wire 60, which may be referred to as an internal conductor; and to the sleeve 26 which may be referred to as an external conductor. In particular, the power source 90 provides a negative terminal 92 which is connected via a wire or the like to the pillow block 70 which is electrically conductive and connected to the sleeve 26 through the bearing 76. Likewise, a wire 96 connects the negative terminal to the insulated wire 60. This is accomplished by providing walls 100 which extend upwardly from the base 72 and which provide screw-eyelets 102 that are axially aligned with the center of the cannister assembly 24. One end of the insulated wire 60 is connected to a tension device 104 through swivel terminals 106. The power source 90 also includes a positive terminal 110 which is connected to the stent 12 via a wire 112 through the conductive pad 58 of the stent holder 54.

In operation, once the cannister assembly 24 is assembled to the pillow block 70 and the appropriate electrical connections are made, the drive motor 80 is energized to initiate rotation of the cannister assembly 24 at a speed of about ⅛ revolutions per minute. As the drive motor 80 rotates the shaft 82, the sheave 84, through the drive belt 86, supplies a rotational force to the cannister assembly 24 such that the solution 64 is evenly distributed in and about the stent 12. As soon as the rotation process is started, the power source 90 is energized to begin transplantation of the endothelial cells within the solution 64 on to the inner and outer surfaces of the stent 12. It will also be appreciated that the surface between the interleaved wires are also covered by the solution 64 and seeded thereto. The tension device 84 and the swivel terminals 106 permit rotation of the insulated conductor 60 without applying excessive rotational forces thereto. A similar arrangement could be used for the wire 112; however, it is anticipated that only 1 to 4 turns of the cannister assembly 24 will be needed to complete seeding of the stent 12. As such, risk of overflexing the wire 112 is minimal.

Figure 3:
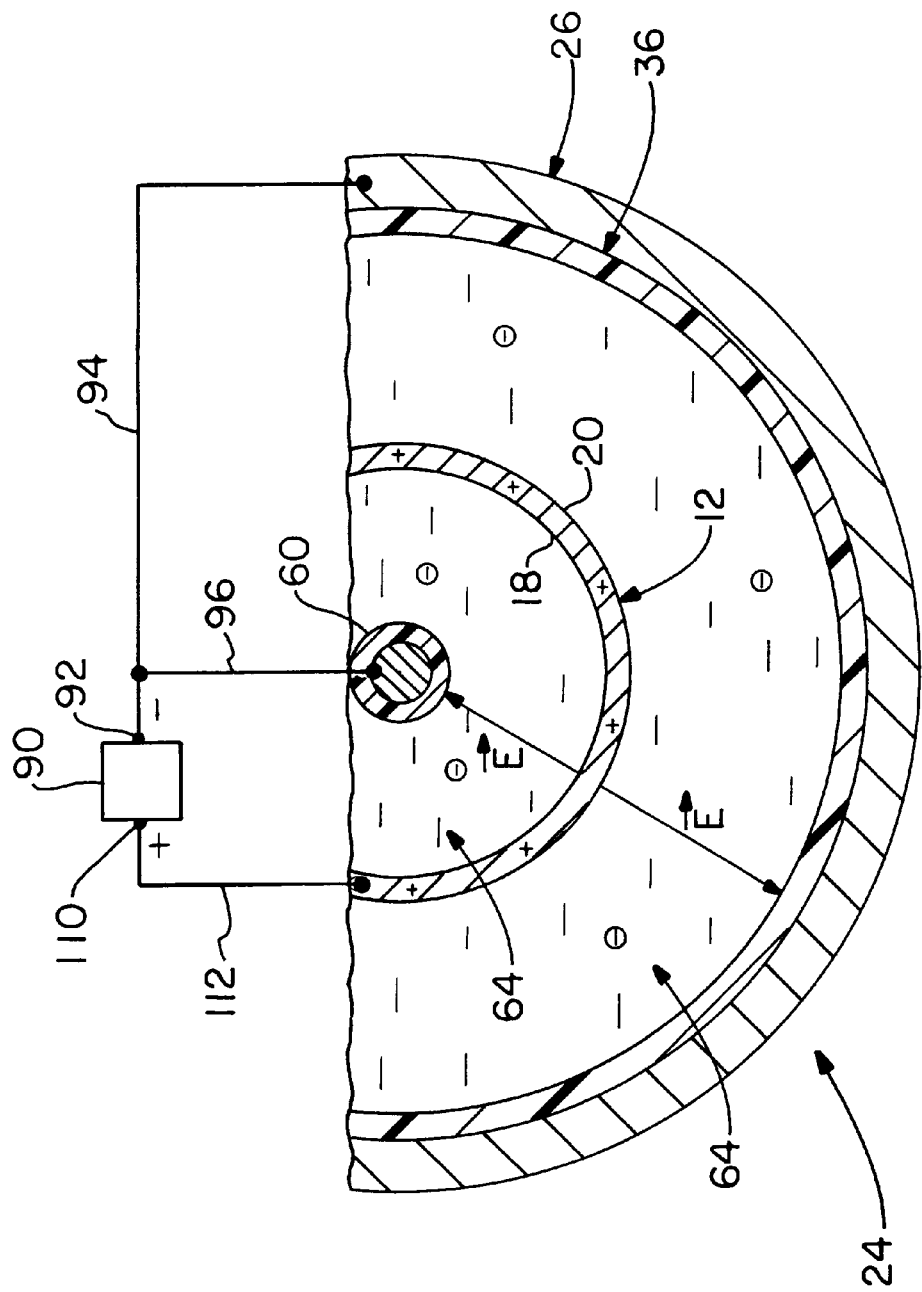
FIG. 3 is a schematic representation showing application of the electric fields to the stent material.

As best seen in FIG. 3, application of an electrical potential between the stent 12 and the insulated wire 60 generates an electric field therebetween. The endothelial cells, which are naturally negatively charged, are attracted to the stent material which is temporarily provided with a positive charge. Likewise, when a negative electrical potential is applied between the sleeve 26 and the stent 12, an electric field is generated therebetween and the stent 12 is disposed with a positive charge to attract the naturally occurring negative endothelial cells.

It is theorized that application of the negative charge to the internal conductor and the external conductor maybe applied separately or simultaneously to facilitate adhesion of the endothelial cells to all the stent surfaces. Inducing the electric field within the cylindrical capacitor arrangement comprising the external conductor, the stent and the internal conductor is accomplished by virtue of the dielectric materials provided by the insulator tube 36 and the insulation provided by the wire 60. Use of the dielectric materials ensure that the stent 12 is spaced apart from the internal and external conductors. Use of the dielectric material also ensures that an electric field is generated through the solution without adversely damaging the endothelial cells. This electric field phenomena within the apparatus 10 creates or induces a positive surface charge on the stent 12 to enhance endothelial cell adhesion and morphological maturation. The induced surface charge dissipates immediately upon removal of the electrical potential. It is believed that optimum seeding or adhesion of the endothelial cells to the stent is obtained by applying a voltage up to 20 volts during a transplantation time of about 8 to 16 minutes. Of course, different voltages and transplantation times may be adjusted to accommodate different stent designs. The power source 90 may also be configured to simultaneously apply 100 µsecond square wave high voltage pulses up to about 2000 volts in varying patterns to facilitate the transfection of any genetically engineered material into the endothelial cells. Once again, the application of pulses and the timing of the square waves may be adjusted according to the particular stent to be seeded.

It is believed that the high voltage pulses cause the cells or the membrane of the cells to become permeable (localized) to exogenous molecules. The permeability is reversible as long as the electric field magnitude and duration do not exceed a critical limit, otherwise cellular death will occur. This method of creating passages (pores) for exogenous material by an electric field has been termed "electroporation." The exact cause of this permeability is not clear at this time. It is believed that the electric fields cause disruption in the lipid bi-layer of cellular membrane directly. Another theory suggests that the acting bundles forming the sidoskeleton may cause protrusions through the cell membrane under the electric field forces. In any event, an endothelial cell under influence of the high energy electric field becomes locally permeable along its membrane to exogenous material (foreign DNA).

Once at least one revolution of the cannister assembly 24 has taken place, the application of the electrical potential is ceased and the operation of the motor is discontinued. At this time, the cannister assembly 24 is removed from the pillow block 70 and the stent 12 is likewise removed from the cannister assembly. The stent 12 is then slightly contracted and re-attached to the balloon catheter for implantation.

Based upon the foregoing disclosure of the structure and method of use for the apparatus 10, several advantages are readily apparent. The apparatus 10 creates an induced temporary surface charge upon the stent 12 such that in conjunction with the electric field mobility of the endothelial cells, adhesion thereof and morphological maturation upon the stent surfaces is obtained. Additionally, the simultaneous high energy electric fields transfect the endothelial cells within a clinically acceptable time prior to implantation. Current techniques require a separate transfection procedure prior to the transplantation and require an adhesive protein coating on the stent surface to enhance endothelial cell adhesion and morphologic maturation. Use of the present invention precludes the need to provide the adhesive protein coating upon the stent. Moreover, prior methods of adhesive protein coating required a cell culture period anywhere from 2 hours up to 3 days to allow morphologic maturation of the adherent cells. Thus, the advantage of the present invention is that it does not adversely alter the stent material. In other words, it does not create a more thrombogenic surface. Additionally, the present invention is advantageous in that seeding and electroporation can be accomplished in the operating room in a clinically acceptable time of less than 20 minutes. Still another advantage of the present invention is that the entire surface of the stent is seeded. Although the outer surface of the stent is embedded into the lumen wall of the artery or vein, it is believed that the adhesion of endothelial cells to the outer surfaces and intristicies of the stent 12 facilitate its acceptance and reduce the failure rate thereof.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of true scope and breadth of the invention, reference should be made to the following claims.

What is claimed is:

1. An apparatus for modifying an intravascular stent with material contained in a solution, comprising:
   an external conductor;
   an insulator received within said external conductor;
   means for suspending the stent in a spaced apart position within said insulator, said insulator receiving the solution which freely flows in and around the stent; and
   a power source for generating an electrical field between the stent and said external conductor so that the electrical charge on the stent is temporarily altered to modify the stent with the material in the solution.

2. The apparatus according to claim 1, further comprising:
   an internal conductor concentrically positioned inside the stent and electrically connected to said power source, wherein both inner and outer surfaces of the stent are temporarily altered.

3. The apparatus according to claim 2, further comprising:
   means for rotating said external conductor as said power source generates said electrical field.

4. The apparatus according to claim 2, wherein the solution contains endothelial cells and said power source applies a voltage of up to about 20 volts between the stent and at least either said external conductor or said internal conductor.

5. The apparatus according to claim 2, wherein the solution contains foreign DNA to be transfected into the endothelial cells to be transplanted on to the surface of the stent and said power source applies a voltage of up to about 2000 volts between the stent and at least either said external conductor or said internal conductor.

6. The apparatus according to claim 2, further comprising:
a pair of insulated end caps; each having a conductive stent holder in an offset position, and a center aperture for receiving said internal conductor;
said external conductor provided as a sleeve which frictionally receives said insulator, wherein said end caps are sealingly disposed at each end of said sleeve, so that the stent is at least slightly expanded.

7. The apparatus according to claim 6, wherein said stent holder has a slit at one end to carry an end of the stent and a conductive cap at an opposite end extending through said insulated end cap for connection to said power source.

8. The apparatus according to claim 6, wherein said external conductor is rotatably receivable in a pillow block and rotated by a motor as said electrical field is applied.

9. An apparatus for modifying an intravascular stent with material to minimize failure rates after implantation, comprising:
an external conductor sleeve;
an insulating tube held within said external conductor sleeve;
a pair of insulated end caps, each detachably securable over each end of said insulating tube, each said insulated cap having a substantially centered aperture therethrough and a stent holder extending transversely therefrom to hold opposite ends of the stent therebetween, wherein the insulated end caps hold a solution containing the material which includes at least endothelial cells inside the insulating tube to surround exposed surfaces of the stent;
an insulated internal conductor receivable within the stent and through said apertures; and
a power source for generating an electrical field between the stent and said external conductor and between the stent and the internal conductor to temporarily alter the electrical charge of the stent to attract and adhere the desired material thereto.

10. The apparatus according to claim 9, wherein said stent holders are provided in an off-center position to hold the stent in a spaced apart position from said insulating tube and from said insulated internal conductor.

11. The apparatus according to claim 10, further comprising:
means for rotating said external conductor sleeve as said electrical field is applied to evenly distribute the solution around the stent and evenly distribute the material to the stent.

12. The apparatus according to claim 10, wherein the solution contains endothelial cells and said power source applies a voltage of up to about 20 volts between the stent and at least either said external conductor or said internal conductor.

13. The apparatus according to claim 10, wherein the solution contains foreign DNA to be transfected into the endothelial cells to be transplanted on to the surface of the stent and said power source applies a voltage of up to about 2000 volts between the stent and at least either said external conductor or said internal conductor.

14. An apparatus for modifying an intravascular stent with material contained in a solution, comprising:

a canister assembly for holding the intravascular stent in a suspended position to allow the solution to contact substantially all inner and outer surfaces of the intravascular stent;
a conductor proximally associated with said cannister assembly; and
a power source for generating an electrical field between the stent and said conductor to temporarily alter the electrical charge of the stent to attract and adhere the desired material thereto.

15. A method for incorporating material on the inner and outer surfaces of an intravascular stent, comprising the steps of:
suspending the intravascular stent in a container;
filling said container with a solution containing the material, wherein said solution contacts the inner and outer surfaces of the stent;
proximally positioning a conductor adjacent the stent;
connecting the stent and said conductor to a power source; and
temporarily applying an electrical potential with said power source between the intravascular stent and the conductor to alter the surface charge of the stent thereby attracting and incorporating the material onto the intravascular stent.

16. The method according to claim 15, further comprising the steps of:
providing said container with an outer sleeve having an insulated tube received therein.

17. The method according to claim 16, further comprising the steps of:
positioning insulated end caps at each end of said container, each said end cap having a stent holder extending transversely into said container; and
detachably mounting each end of the stent to a respective stent holder so that the stent is spaced apart from the container to allow the solution to contact the inner and outer surfaces of the stent.

18. The method according to claim 17, further comprising the step of:
rotating said container as said electrical potential is applied.

19. The method according to claim 18, further comprising the step of:
concentrically positioning said conductor through said end caps and centrally positioned inside said stent.

20. The method according to claim 18, further comprising the step of:
concentrically positioning said conductor around said container and outside the stent.

21. The method according to claim 18, further comprising the step of:
applying a voltage of up to about 20 volts between the stent and said conductor with said power source, wherein the solution contains endothelial cells.

22. The method according to claim 18, further comprising the step of:
applying a voltage of up to about 2000 volts between the stent and said conductor with said power source, wherein the solution contains foreign DNA to be transfected into the endothelial cells to be transplanted on to the surface of the stent.

* * * * *